· US006880410B2

United States Patent
Drahm et al.

(10) Patent No.: US 6,880,410 B2
(45) Date of Patent: Apr. 19, 2005

(54) TRANSDUCER AND METHOD FOR MEASURING A FLUID FLOWING IN A PIPE

(75) Inventors: Wolfgang Drahm, Erding (DE); Alfred Rieder, Landshut (DE)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 10/386,930

(22) Filed: Mar. 13, 2003

(65) Prior Publication Data

US 2003/0230150 A1 Dec. 18, 2003

Related U.S. Application Data

(60) Provisional application No. 60/363,850, filed on Mar. 14, 2002.

(30) Foreign Application Priority Data

Mar. 14, 2002 (EP) .............................. 02005868

(51) Int. Cl.$^7$ ................................. G01F 1/84
(52) U.S. Cl. ................................. 73/861.357
(58) Field of Search .................... 73/861, 861.04, 73/861.355, 861.356, 861.357

(56) References Cited

U.S. PATENT DOCUMENTS

| | | | |
|---|---|---|---|
| 4,420,983 A | | 12/1983 | Langdon |
| 5,458,005 A | * | 10/1995 | Perelshteyn .............. 73/861.34 |
| 6,318,156 B1 | | 11/2001 | Dutton et al. |
| 6,487,917 B1 | * | 12/2002 | Van Cleve et al. ..... 73/861.357 |

OTHER PUBLICATIONS

Patent Abstracts of Japan, vol. 1997, No. 06, Jun. 30, 1997, JP 09053969, Oscillatory Measuring Apparatus.
Patent Abstracts of Japan, vol. 1999, No. 01, Jan. 29, 1999, JP 10281846, Polyphase Flowmeter by Pattern Recognition Method . . . Flowmeter.

* cited by examiner

*Primary Examiner*—Edward Lefkowitz
*Assistant Examiner*—Corey D. Mack
(74) *Attorney, Agent, or Firm*—Bacon & Thomas

(57) ABSTRACT

The transducer serves to generate a measurement signal corresponding to at least one physical parameter of a fluid flowing in a pipe. It comprises a flow tube of predeterminable lumen for conducting the fluid which communicates with the pipe at the inlet and outlet ends. In operation, an excitation assembly causes reactions, particularly reaction forces, in the fluid within the at least one flow tube in a non-invasive manner, which are sensed and converted into measurement signals representative thereof by means of a sensor arrangement. To obtain as axisymmetric a density distribution in the fluid as possible, means are provided in an inlet area of the transducer or at least in the vicinity thereof which cause a swirl in the entering fluid and, thus, a rotational motion in the fluid within the flow-tube lumen about an axis of rotation lying in the direction of fluid flow. As a result of the axisymmetric density distribution thus produced, the transducer provides accurate and robust measurement signals even in the case of inhomogeneous, particularly multiphase, fluids, and substantially independently of the mounting position of the flow tube.

10 Claims, 6 Drawing Sheets

TRANSDUCER AND METHOD FOR MEASURING A FLUID FLOWING IN A PIPE

This application is based on Provisional Application No. 60/363,850, filed on Mar. 14, 2002.

FIELD OF THE INVENTION

This invention relates to a transducer and a method for measuring at least one physical parameter, particularly a mass flow rate and/or a density and/or a viscosity, of a fluid flowing in a pipe, particularly of a multiphase fluid, in a non-invasive manner.

BACKGROUND OF THE INVENTION

In process-measurement and automation technology, physical parameters of a fluid flowing in a pipe, such as mass flow rate, density, and/or viscosity, are frequently measured by means of meters which, using a vibratory transducer traversed by the fluid and a measuring and control circuit connected thereto, induce reaction forces, such as Coriolis forces corresponding to the mass flow rate, inertial forces corresponding to the density, or friction forces corresponding to the viscosity, in the fluid in a non-invasive manner, and derives therefrom a measurement signal representing the respective mass flow rate, viscosity, and/or density of the fluid.

Such vibratory transducers are disclosed, for example, in WO-A 01/33174, WO-A 00/57141, WO-A 98/07009, WO-A 95/16897, WO-A 88/03261, U.S. Pat. No. 6,006,609, U.S. Pat. No. 5,796,011, U.S. Pat. No. 5,301,557, U.S. Pat. No. 4,876,898, U.S. Pat. No. 4,524,610, EP-A 553 939, or EP-A 1 001 254.

To conduct the fluid, each of the transducers comprises at least one flow tube held in a support frame and having a bent or straight tube segment which in operation, driven by an electromechanical excitation assembly, is caused to vibrate in order to produce the above-mentioned reaction forces. To sense vibrations of the tube segment, particularly inlet-side and outlet-side vibrations, the transducers each comprise a sensor arrangement which responds to motions of the tube segment.

Aside from such vibration transducers, electromagnetic transducers or transducers evaluating the transit time of ultrasonic waves transmitted in the direction of fluid flow, particularly transducers based on the Doppler principle, are frequently used in process-measurement and automation technology for in-line measurements. Since the basic construction and the operation of such electromagnetic transducers are sufficiently described in EP-A 1 039 269, U.S. Pat. No. 6,031,740, U.S. Pat. No. 5,540,103, U.S. Pat. No. 5,351,554, or U.S. Pat. No. 4,563,904, for example, and the basic construction and the operation of such ultrasonic transducers are sufficiently described in U.S. Pat. No. 6,397,683, U.S. Pat. No. 6,330,831, U.S. Pat. No. 6,293,156, U.S. Pat. No. 6,189,389, U.S. Pat. No. 5,531,124, U.S. Pat. No. 5,463,905, U.S. Pat. No. 5,131,279, or U.S. Pat. No. 4,787,252, for example, a detailed explanation of these principles of measurement can be dispensed with at this point.

For clarification it should be mentioned that within the scope of the invention, "non-invasive transducers" means those transducers which do not comprise any flow bodies which are immersed in the fluid and serve to influence its flow for the purpose of producing measurement effects. By contrast, within the scope of this invention, those transducers which, in order to measure the fluid, produce vortices in the fluid flow or use baffles, bluff bodies, floats, or orifice plates are regarded as "invasive transducers". Such invasive transducers are also familiar to those skilled in the art and are sufficiently described, for example, in WO-A 01/20282, WO-A 97/22855, U.S. Pat. No. 6,352,000, U.S. Pat. No. 6,003,384, U.S. Pat. No. 5,939,643, U.S. Pat. No. 5,922,970, U.S. Pat. No. 5,458,005, U.S. Pat. No. 4,716,770, U.S. Pat. No. 4,476,728, U.S. Pat. No. 4,445,388, U.S. Pat. No. 4,437,350, U.S. Pat. No. 4,339,957, EP-A 690 292, EP-A 684,458, DE-A 39 04 224, DE-A 38 10 889, DE-A 17 98 360, or DE-A 100 01 165.

During the use of non-invasive in-line transducers it turned out that in the case of inhomogeneous fluids, particularly of multiphase fluids, the measurement signals produced, in spite of the viscosity and density being maintained virtually constant, particularly under laboratory conditions, are subject to considerable nonreproducible variations and may thus become practically unusable for the measurement of the respective physical parameter.

In U.S. Pat. No. 4,524,610, a possible cause of this problem in the operation of vibratory transducers is indicated, namely the fact that parasitic inhomogeneities introduced by the fluid into the flow tube, such as gas bubbles, may be trapped at the inside wall of the tube. To avoid this problem, it is proposed to install the transducer so that the straight flow tube is in an essentially vertical position, so that the trapping of such parasitic, particularly gaseous, inhomogeneities is prevented.

This, however, is a very specific solution which is only conditionally realizable, particularly in industrial process measurement technology. On the one hand, the pipe into which the transducer is to be inserted would have to be adapted to the transducer and not vice versa, which probably cannot be conveyed to the user. On the other hand, the flow tubes, as mentioned, may also have a curved shape, so that the problem cannot be solved by adapting the mounting position, either. It also turned out that the above-described distortions of the measurement signal cannot be appreciably reduced even if a vertically installed straight flow tube is used. Variations in the measurement signal in the presence of a flowing fluid cannot be prevented in this manner, either.

SUMMARY OF THE INVENTION

It is therefore an object of the invention to provide a method and a transducer which even in the case of inhomogeneous, particularly multiphase, fluids provides accurate, but at least easily reproducible and highly robust measurement signals substantially regardless of the instantaneous density distribution within the fluid flowing in the connected pipe, but particularly substantially regardless of the concentration of any parasitic inhomogeneities, and substantially regardless of the mounting position of the flow tube.

To attain this object, the invention provides a method of measuring at least one physical parameter, particularly a mass flow rate and/or a density and/or a viscosity, of a fluid flowing in a pipe, the method comprising the steps of: causing a swirl in a flowing fluid about a swirl axis aligned with a direction of fluid flow for forcing a density distribution in the fluid which is as symmetric with respect to the swirl axis as possible; causing the fluid rotating about the swirl axis to flow through at least one flow tube of a non-invasive transducer inserted into the pipe for producing reactions in the fluid corresponding to the parameter to be measured; and sensing reactions in the fluid for generating at least one measurement signal influenced by the parameter to be measured.

Furthermore, the invention provides a transducer for generating a measurement signal corresponding to at least one physical parameter of a fluid flowing in a pipe, the transducer comprising: at least one flow tube of predetermined lumen for conducting the fluid, which flow tube communicates at its inlet and outlet ends with the pipe; an excitation assembly for causing reactions in the fluid within the at least one flow tube, the reactions in the fluid being produced in a non-invasive manner; and a sensor arrangement for sensing the reactions in the fluid and for generating the measurement signal, with means provided in an inlet area of the transducer or at least in the vicinity thereof which cause a swirl in the entering fluid and, thus, a rotational motion in the fluid flowing within the flow-tube lumen relative to the flow tube about an axis of rotation lying in the direction of fluid flow.

In a development, the invention provides a meter for measuring at least one physical parameter of a fluid flowing in a pipe, particularly a meter suitable for implementing the method according to the invention, which comprises the transducer according to the invention.

In a embodiment of the method of the invention, the fluid-conducting pipe is vibrated for producing reaction forces in the fluid to be measured which correspond to the parameter to be measured and react on the vibrating flow tube, and vibrations of the flow tube are sensed to generate the at least one measurement signal.

In a first embodiment of the transducer of the invention, the at least one flow tube communicates with the pipe via an inlet tube section and an outlet tube section, and the means for causing the swirl are at least partly disposed within the inlet tube section.

In a second embodiment of the transducer of the invention, the means for causing the swirl are at least partly disposed within the at least one flow tube.

In a third embodiment of the transducer of the invention, the means for causing the swirl are at least partly disposed within the pipe.

In a fourth embodiment of the transducer of the invention, the means for causing the swirl comprise at least one turbulator extending into the flowing fluid, particularly a stationary turbulator.

In a fifth embodiment of the transducer of the invention, the turbulator comprises at least one baffle extending into the flowing fluid.

In a sixth embodiment of the transducer of the invention, the turbulator has the form of propeller.

In a seventh embodiment of the transducer of the invention, the turbulator has the form of a helix.

In an eighth embodiment of the transducer of the invention, the turbulator is helicoidal.

In a ninth embodiment of the transducer of the invention, the means for causing the swirl are fixed to the inside wall of the inlet tube section and/or to the inside wall of the flow tube.

In a tenth embodiment of the transducer of the invention, the means for causing the swirl are held against the inside wall of the inlet tube section and/or against the inside wall of the flow tube.

In an eleventh embodiment of the transducer of the invention, the means for causing the swirl are designed as a rifling formed in the inside wall of the inlet tube section and/or in the inside wall of the flow tube.

In a twelfth embodiment of the transducer of the invention, the means for causing the swirl have an effective length in the direction of flow which is at least equal to a nominal diameter of the pipe.

In a thirteenth embodiment of the invention, the transducer is installed in an essentially horizontal pipe.

In a fourteenth embodiment of the invention, the transducer is installed in an essentially vertical pipe.

In a fifteenth embodiment of the transducer of the invention, in order to produce reaction forces acting in the fluid, the at least one flow tube is vibrated by means of the excitation assembly, and vibrations of the flow tube are sensed by means of the sensor arrangement.

In a first embodiment of the meter of the invention, the physical parameter to be measured is a mass flow rate.

In a second embodiment of the meter of the invention, the physical parameter to be measured is a density.

In a third embodiment of the meter of the invention, the physical parameter to be measured is a viscosity.

A basic idea of the invention is to induce in the fluid, by means of the rotational motion about the swirl axis, centrifugal forces such that at least within the flow-tube lumen, a density distribution is forced which is as symmetric in respect of the swirl axis of the rotating "fluid column" as possible and, thus, largely reproducible. Compared to the above-described nonreproducible variations, a possible slight measurement error, particularly a slight error in the measured density value, which is to be expected mainly in the case of liquids with parasitic gaseous inhomogeneities because such gas occlusions are concentrated at the center of the flow-tube lumen as a result of the centrifugal forces can be considered negligibly small.

The invention is predicated particularly on the recognition that the above-described variations of the measurement signals are caused not only by the fact that gas bubbles, for example, are trapped at the inside wall of the flow tube, but particularly by the fact that this takes place essentially chaotically and, hence, in a nonreproducible or unpredictable manner. In other words, if conventional transducers with straight or slightly curved flow tubes are used for inhomogeneous, particularly multiphase, fluids, the variations of the measurement signals can be attributed largely to the essentially chaotic distribution of inhomogeneities in the fluid, such as entrained gas bubbles, and, thus, to a constantly varying, but practically undetectable density distribution within the fluid in the flow-tube lumen.

One advantage of the invention, particularly of the method according to the invention, is that it can be used in practically all known in-line transducers, particularly for all flow measurement principles, and, consequently, both in vibratory transducers and, for instance, in electromagnetic or ultrasonic transducers.

BRIEF DESCRIPTION OF THE DRAWINGS

The invention and further advantages will become more apparent from the following description of embodiments taken in conjunction with the accompanying drawings. Like parts are designated by like reference characters throughout the various figures of the drawings; reference characters that were already assigned have been omitted in subsequent figures if this contributes to clarity. In the drawings.

DETAILED DESCRIPTION OF EXEMPLARY EMBODIMENTS

Figure 1:
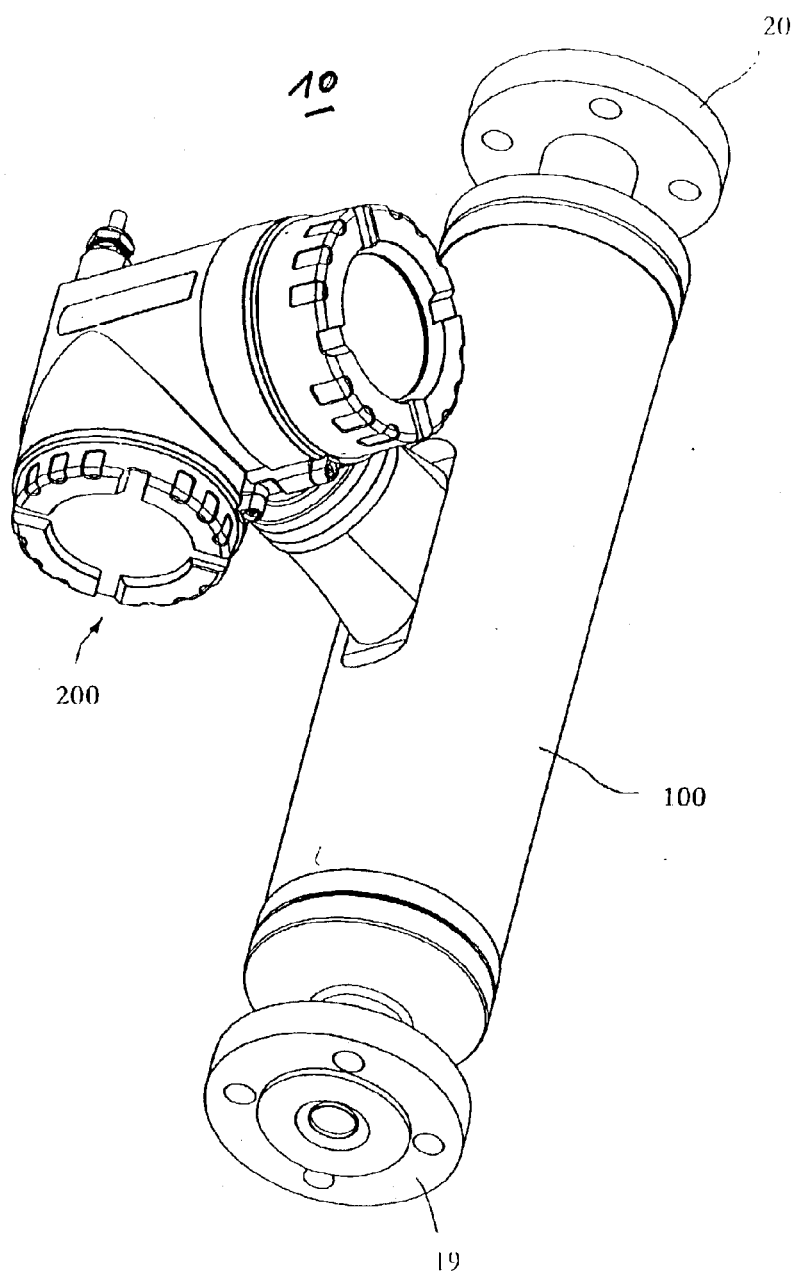
FIG. 1 is a perspective view of a meter for measuring at least one physical parameter of a fluid flowing in a pipe.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the intended claims.

FIG. 1 shows schematically a meter with a transducer 10, preferably housed in a transducer case 100, and with meter electronics (not shown), housed in an electronics case 200 and electrically connected to transducer 10. The meter serves in particular to sense a physical parameter of a fluid flowing in a pipe (not shown), particularly a mass flow rate m and/or a density ρ and/or a viscosity η, and to map it into a measured value representing this parameter. The meter can also be used to measure a volumetric flow rate of the fluid, for example.

To that end, in operation, reactions are produced in the fluid in a non-invasive manner by means of the meter-electronics-driven transducer 10 which are dependent on the parameter to be measured and react on transducer 10 in a measurable manner, i.e., which can be detected using sensor technology and converted into useful input signals for subsequent evaluation electronics. Such reactions may be, for instance, volumetric-flow-rate-dependent, electromagnetically generated voltages, mass-flow-rate-dependent Coriolis forces, density-dependent mass inertial forces, and/or viscosity-dependent friction or damping forces, etc. "Producing reactions in the fluid in a non-invasive manner", as already indicated at the beginning, means here that the sensed reactions, which correspond to the parameter to be measured, are produced without any flow bodies additionally immersed in and changing the fluid flow.

For the case where the meter is designed to be coupled to a Fieldbus, the, preferably programmable, meter electronics include a suitable communication interface for data communication, e.g., for the transmission of the measurement data to a higher-level stored program control or a higher-level process control system.

Figure 2:
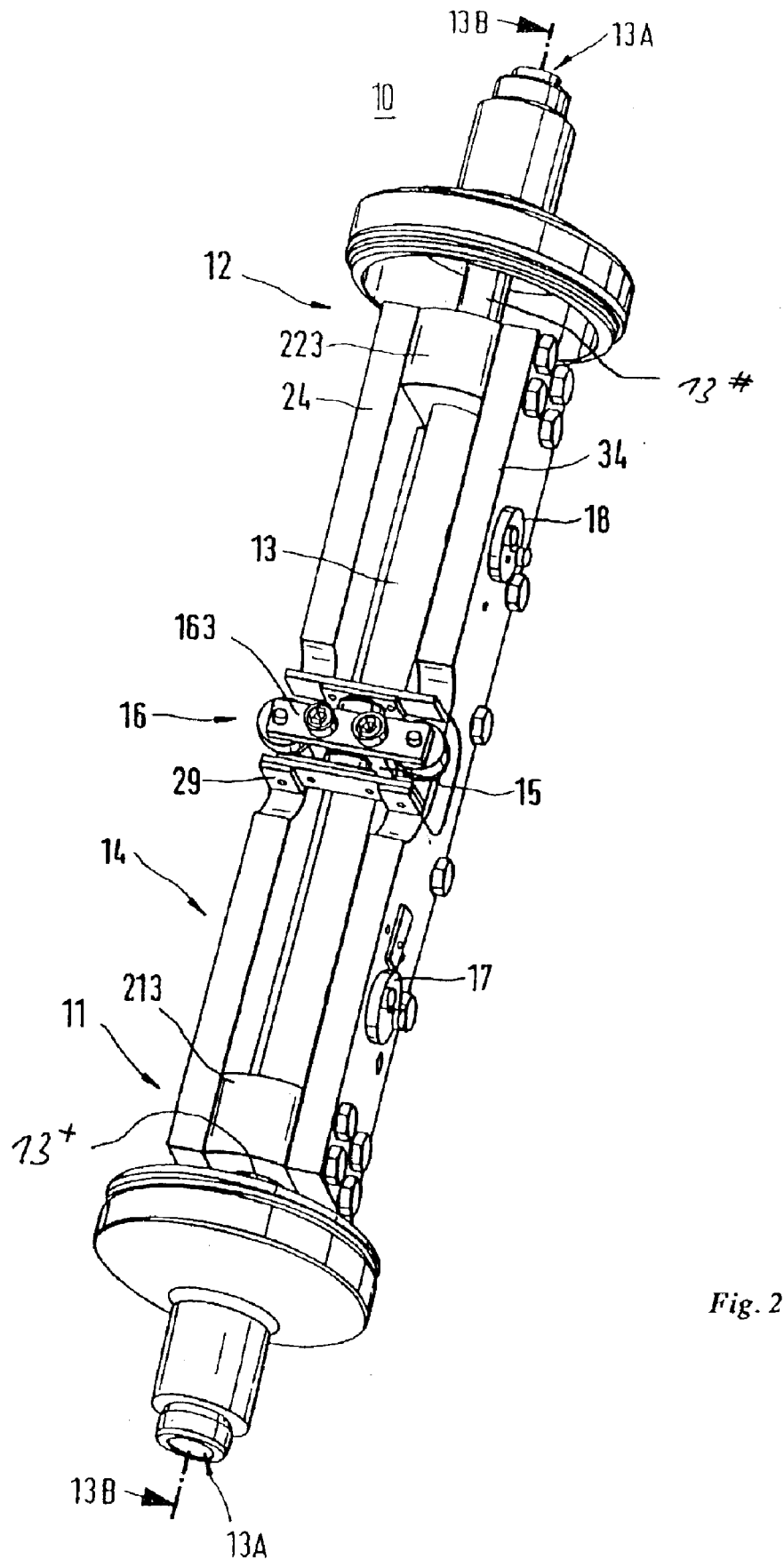
FIG. 2 is a first perspective view of an embodiment of a vibratory transducer suitable for the meter of FIG. 1.
Figure 3:
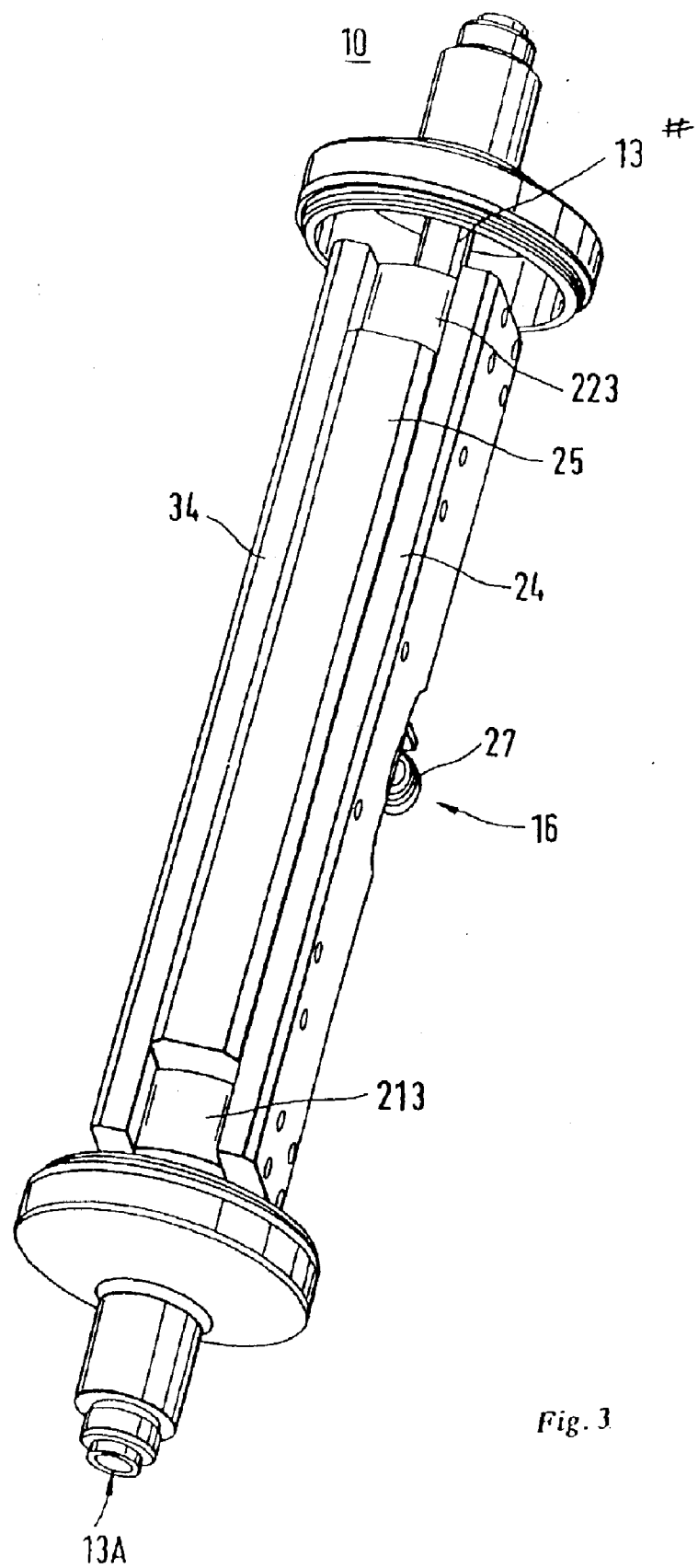
FIG. 3 is a second perspective view of the transducer of FIG. 2.

FIGS. 2 and 3 show an embodiment of a transducer 10 in the form of a physical-to-electrical vibratory transducer assembly. The construction of such a transducer assembly is described in detail in U.S. Pat. No. 6,006,609, for example. Such transducers are already used in commercially available Coriolis mass flowmeter-densimeters as are offered by the applicant with its "PROMASS I" series, for example.

To conduct the fluid to be measured, transducer 10 comprises at least one flow tube 13 of a predeterminable, elastically deformable lumen 13A and a predeterminable nominal diameter, which has an inlet end 11 and an outlet end 12. "Elastic deformation" of lumen 13A as used herein means that in order to produce reaction forces within the fluid, i.e., reaction forces descriptive of the fluid, namely shear or friction forces, but also Coriolis forces and/or mass inertial forces, during operation of transducer 10, a three-dimensional shape and/or a spatial position of lumen 13A are changed in a predeterminable cyclic manner, particularly periodically, within an elasticity range of flow tube 13; see, for example, U.S. Pat. No. 4,801,897, U.S. Pat. No. 5,648,616, U.S. Pat. No. 5,796,011, and/or U.S. Pat. No. 6,006,609.

At this point is should be noted that instead of a transducer according to the embodiment of FIGS. 2 and 3, virtually any of the transducers for Coriolis flowmeter-densimeters which are known to the person skilled in the art, particularly a flexural mode transducer with a bent or straight flow tube vibrating exclusively or at least in part in a flexural mode, can be used for implementing the invention. Further implementations of transducer assemblies suitable for use as transducer 10 are described, for example, in U.S. Pat. Nos. 5,301,557, 5,357,811, 5,557,973, 5,602,345, 5,648,616, or 5,796,011, which are incorporated herein by reference. It is also possible to use conventional electromagnetic or ultrasonic transducers, for example. Materials suited for flow tube 13, here an essentially straight tube, are titanium alloys, for example. Instead of titanium alloys, other materials commonly used for such flow tubes, particularly for bent tubes, such as stainless steel, tantalum, or zirconium, may be employed.

Flow tube 13, which communicates with the fluid-conducting pipe via an inlet tube section 13$^+$ and an outlet tube section 13$^\#$ in the usual manner, is clamped in a rigid support frame 14, particularly in a flexurally and torsionally stiff frame, so as to be capable of vibratory motion, the support frame preferably being enclosed by a transducer case 100. Flow tube 13 as well as inlet and outlet tube sections 13$^+$, 13$^\#$ preferably are integrally formed from a single tubular semifinished product; if necessary, they may, of course, be of multipart construction.

Support frame 14 is fixed to inlet tube section 13$^+$ by means of an inlet plate 213 and to outlet tube section 13$^\#$ by means of an outlet plate 223, the two plates being penetrated by respective extension pieces of flow tube 13. Support frame 14 has a first side plate 24 and a second side plate 34, which are fixed to inlet plate 213 and outlet plate 223 in such a way as to extend essentially parallel to and in spaced relationship from flow tube 13; see FIGS. 2 and 3. Thus, facing side surfaces of the two side plates 24, 34 are also parallel to each other.

Advantageously, a longitudinal bar 25 serving as a balancing mass for absorbing vibrations of flow tube 13 is secured to side plates 24, 34 in spaced relationship from flow tube 13. As shown in FIG. 3, longitudinal bar 25 extends essentially parallel to the entire oscillable length of flow tube 13. If necessary, longitudinal bar 25 may, of course, be shorter.

Thus, support frame 14 with the two side plates 24, 34, inlet plate 213, outlet plate 223, and the optional longitudinal bar 25 has a longitudinal axis of gravity which is essentially parallel to a central flow tube axis 13B, which joins inlet end 11 and outlet end 12.

In FIGS. 2 and 3, it is indicated by the heads of the screws shown that the aforementioned fixing of side plates 24, 34 to inlet plate 213, to outlet plate 223, and to longitudinal bar 25 may be done by screwing; it is also possible to use other suitable forms of fastening familiar to those skilled in the art.

If transducer 10 is to be nonpermanently connected with the pipe, preferably a first flange 19 and a second flange 20 are formed on inlet tube section 13$^+$ and outlet tube section 13$^\#$, respectively, see FIG. 1; instead of flanges 19, 20, so-called Triclamp connections, for example, may be used to provide the nonpermanent connection with the pipe, as indicated in FIG. 2 or 3. If necessary, however, flow tube 13 may also be connected with the pipe directly, e.g., by welding or brazing.

To produce the above-mentioned reaction forces in the fluid, during operation of transducer 10, flow tube 13, driven by an electromechanical excitation assembly 16 coupled to the flow tube, is caused to vibrate in the so-called useful mode at a predeterminable frequency, particularly at a natural resonance frequency which is also dependent on the density p of the fluid, whereby the flow tube is elastically deformed in a predeterminable manner.

In the embodiment shown, the vibrating flow tube 13, as is usual with such flexural mode transducer assemblies, is spatially, particularly laterally, deflected from a static rest position; the same applies to transducer assemblies in which one or more curved flow tubes perform cantilever vibrations about a corresponding longitudinal axis joining the respective inlet and outlet ends, or to those in which one or more straight flow tubes perform only planar flexural vibrations about their longitudinal axis. For the other case where transducer 10 is a radial mode transducer assembly and the vibrating flow tube is symmetrically deformed in the usual manner as is described, for example, in WO-A 95/16897, the flow tube is essentially left in its static rest position.

Excitation assembly 16 serves to produce an excitation force acting on flow tube 13 by converting electric excitation power supplied from the meter electronics. The excitation power serves virtually only to compensate the power component lost in the vibrating system because of mechanical and fluid friction. To achieve as high an efficiency as possible, the excitation power is preferably adjusted so that essentially the vibrations of flow tube 13 in the useful mode, e.g., those at a lowest resonance frequency, are maintained.

Figure 4:
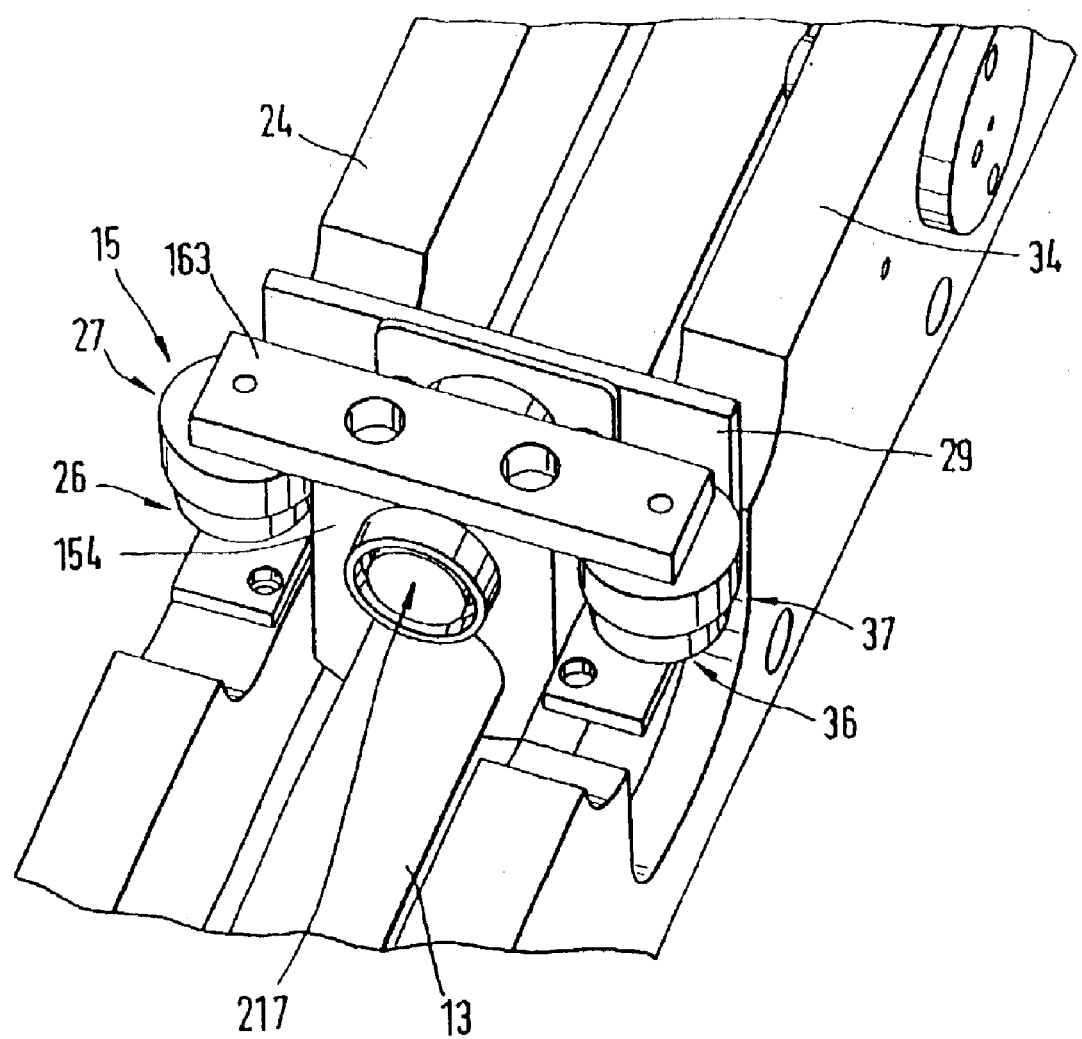
FIG. 4 shows an embodiment of an electromechanical excitation assembly suitable for the transducer of FIGS. 2 and 3.

For the purpose of transmitting the excitation force to flow tube 13, excitation assembly 16, as shown in FIG. 4, has a rigid, electromagnetically and/or electrodynamically driven lever arrangement 15 with a cantilever 154 and a yoke 163, the cantilever 154 being rigidly fixed to flow tube 13. Yoke 163 is rigidly fixed to an end of cantilever 154 remote from flow tube 13, such that it lies above and extends transversely of flow tube 13. Cantilever 154 may be a metal plate, for example, which receives flow tube 13 in a bore. For further suitable implementations of lever arrangement 15, reference is made to the above-mentioned U.S. Pat. No. 6,006,609. As is readily apparent from FIG. 2, lever arrangement 15, here a T-shaped arrangement, is preferably arranged to act on flow tube 13 approximately midway between inlet end 11 and outlet end 12, so that in operation, flow tube 13 will undergo its maximum lateral deflection at its midpoint.

To drive the lever arrangement 15, excitation assembly 16, as shown in FIG. 4, comprises a first excitation coil 26 and an associated first armature 27 of permanent-magnet material as well as a second excitation coil 36 and an associated second armature 37 of permanent-magnet material. The two excitation coils 26 and 36, which are preferably electrically connected in series, are fixed to support frame 14 on both sides of flow tube 13 below yoke 163, particularly nonpermanently, so as to interact in operation with their associated armatures 27 and 37, respectively. If necessary, the two excitation coils 26, 36 may, of course, be connected in parallel.

As shown in FIGS. 2 and 4, the two armatures 27, 37 are fixed to yoke 163 at such a distance from each other that during operation of transducer 10, armature 27 will be penetrated essentially by a magnetic field of excitation coil 26, while armature 37 will be penetrated essentially by a magnetic field of excitation coil 36, so that the two armatures will be moved by the action of corresponding electrodynamic and/or electromagnetic forces.

The motions of armatures 27, 37 produced by the magnetic fields of excitation coils 26, 36 are transmitted by yoke 163 and cantilever 154 to flow tube 13. These motions of armatures 27, 37 are such that yoke 163 is displaced from its rest position alternately in the direction of side plate 24 and in the direction of side plate 34. A corresponding axis of rotation of lever arrangement 15, which is parallel to the above-mentioned central axis 13B of flow tube 13, may pass through cantilever 154, for example.

Particularly in order to hold excitation coils 26, 36 and individual components of a magnetic brake assembly 217, which is described below, support frame 14 further comprises a holder 29 for electromechanical excitation assembly 16. Holder 29 is connected, preferably nonpermanently, with side plates 24, 34.

In the transducer 10 of the embodiment, the lateral deflections of the vibrating flow tube 13, which is firmly clamped at inlet end 11 and outlet end 12, simultaneously cause an elastic deformation of its lumen 13A; this elastic deformation extends virtually over the entire length of flow tube 13.

Furthermore, due to a torque acting on flow tube 13 via lever arrangement 15, torsion is induced at least in sections of flow tube 13 about central axis 13B simultaneously with the lateral deflections, so that the flow tube vibrates in a mixed flexural and torsional mode serving as a useful mode. The torsion of flow tube 13 may be such that the direction of a lateral displacement of the end of cantilever 154 remote from flow tube 13 is either the same as or opposite to that of the lateral deflection of flow tube 13. In other words, flow tube 13 can perform torsional vibrations in a first flexural and torsional mode, corresponding to the former case, or in a second flexural and torsional mode, corresponding to the latter case. In the transducer 10 according to the embodiment, the natural resonance frequency of the second flexural and torsional mode, e.g., 900 Hz, is approximately twice as high as that of the first flexural and torsional mode.

For the case where flow tube 13 is to perform vibrations only in the second flexural and torsional mode, excitation assembly 16 advantageously incorporates a magnetic brake assembly 217 based on the eddy-current principle, which serves to stabilize the position of the axis of rotation. By means of magnetic brake assembly 217 it can thus be ensured that flow tube 13 always vibrates in the second flexural and torsional mode, so that any external disturbing effects on flow tube 13 will not result in a spontaneous change to another flexural and torsional mode, particularly to the first. Details of such a magnetic brake assembly are described in U.S. Pat. No. 6,006,609, for example; furthermore, the use of such magnetic brake assemblies is known from transducers of the aforementioned "PROMASS I" series.

At this point it should be mentioned that in the flow tube 13 deflected in this manner according to the second flexural and torsional mode, the central axis 13B is slightly deformed, so that during the vibrations, this axis spreads a slightly curved surface rather than a plane. Furthermore, a path curve lying in this surface and described by the midpoint of the central axis of the flow tube has the smallest curvature of all path curves described by the central tube axis.

To detect the deformations of flow tube 13, transducer 10 comprises a sensor arrangement with at least a first sensor 17, which provides a first, particularly analog, sensor signal in response to vibrations of flow tube 13. As is usual with such transducers, sensor 17 may be formed, for instance, by an armature of permanent-magnet material which is fixed to flow tube 13 and interacts with a sensor coil held by support frame 14.

Sensor types especially suited for sensor 17 are those which sense the velocity of the deflections of the flow tube based on the electrodynamic principle. It is also possible to use acceleration-measuring electrodynamic or displacement-measuring resistive or optical sensors, or other sensors familiar to those skilled in the art which are suitable for detecting such vibrations.

In a embodiment of the invention, sensor arrangement further comprises a second sensor 18, particularly a sensor identical to the first sensor 17, which second sensor 18 provides a second sensor signal representing vibrations of the flow tube. In this embodiment, the two sensors 17, 18 are positioned at a given distance from each other along flow tube 13, particularly at the same distance from the midpoint of flow tube 13, such that sensor arrangement will detect both inlet-side and outlet-side vibrations of flow tube 13 and provide the corresponding sensor signals.

The first sensor signal and, if present, the second sensor signal, which usually each have a frequency corresponding to the instantaneous vibration frequency of flow tube 13, are fed to the meter electronics (not shown).

To vibrate the flow tube 13, excitation assembly 16 is supplied from meter electronics with a likewise oscillating, unipolar or bipolar excitation current of adjustable amplitude and adjustable frequency, such that in operation, excitation coils 26, 36 are traversed by this current to produce the magnetic field necessary to move armatures 27, 37. Thus, the excitation force required to vibrate flow tube 13 can be monitored and adjusted in amplitude, e.g. by means of a current- and/or voltage-regulator circuit using at least one of the sensor signals, and in frequency, e.g. by means of a phase-locked loop, in the manner familiar to those skilled in the art. The excitation current delivered by the meter electronics is preferably a sinusoidal current, but it may also be a pulsating, triangular, or square-wave alternating current, for example.

As is usual in vibration meters of the kind described herein, the frequency of the excitation current is equal to the predetermined vibration frequency of flow tube 13, and is therefore preferably set at an instantaneous natural resonance frequency of the fluid-carrying flow tube 13.

It should be mentioned that, if the transducer is a non-invasive electromagnetic flow sensor, instead of the excitation assembly shown above, an excitation assembly in the form of a coil assembly will be used in the manner familiar to those skilled in the art, which, when traversed by an excitation current, produces a magnetic field in the fluid flowing in the flow tube. The sensor arrangement will then be an electrode arrangement which picks off a measurement voltage induced in the fluid by means of the above-mentioned magnetic field.

If the transducer is a non-invasive ultrasonic flow sensor, the excitation assembly will be in the form of an ultrasonic transducer which, when traversed by an excitation current, couples ultrasonic waves into the fluid flowing in the flow tube. Then, an ultrasonic transducer will also be used for the sensor arrangement, which extracts ultrasonic waves from the fluid and converts them into a corresponding measurement voltage.

Since the transducer 10 shown in FIGS. 1 to 4 is a multivariable transducer which for detecting, alternately or simultaneously, the mass flow rate, m, of the fluid by means of the two sensor signals and/or the density, $\rho$, by means of the excitation frequency and/or the viscosity, $\eta$, by means of the excitation current, for the further explanation of the invention and for the sake of consistency and clarity, the sensor signals, the excitation current, or the above-mentioned measurement voltages are henceforth classed under the term "measurement signal".

As mentioned, investigations have shown that the measurement signal corresponding to the parameter to be measured, i.e., the first sensor signal or the excitation current, for example, may be influenced to a considerable extent by an instantaneous density distribution in the fluid flowing in flow tube 13, particularly by a concentration and distribution of possible parasitic inhomogeneities.

To improve the measurement signals, particularly to increase their robustness to such inhomogeneities, according to the invention, means are provided in an inlet area of transducer 10 or at least in the vicinity thereof which cause a swirl in the entering fluid, and thus a rotational motion in the fluid within the flow-tube volume about an imaginary axis of rotation lying in the direction of fluid flow. For the case where the flow tube is straight, the imaginary axis of rotation practically coincides with the central flow-tube axis 13B.

Figure 5A:
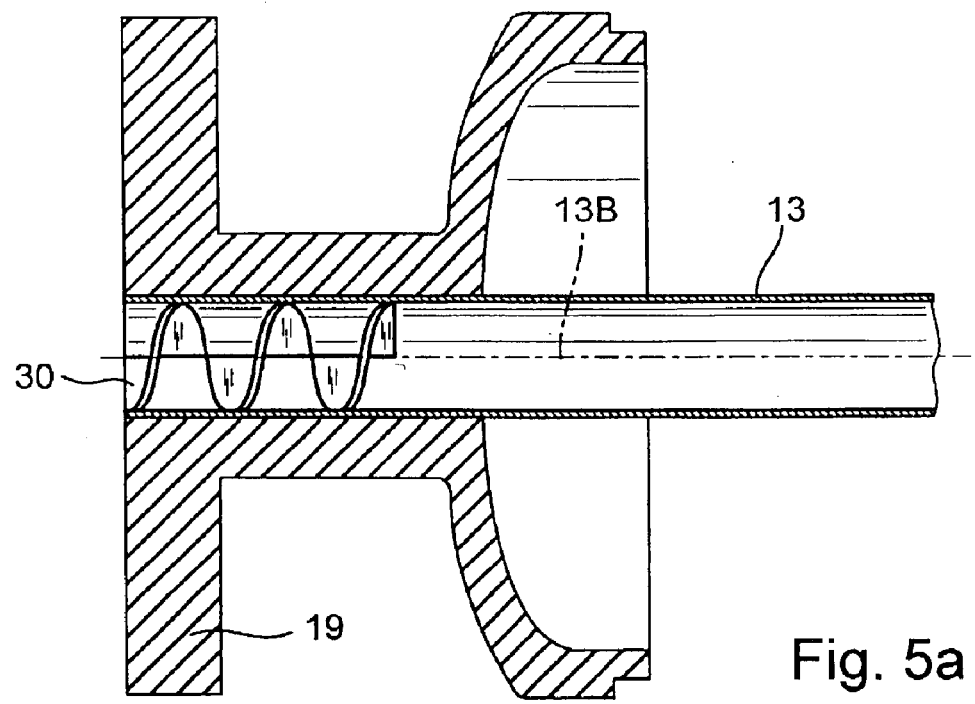
FIGS. 5a to 5d show embodiments of means according to the invention for causing a swirl in the fluid to be measured.
Figure 5B:
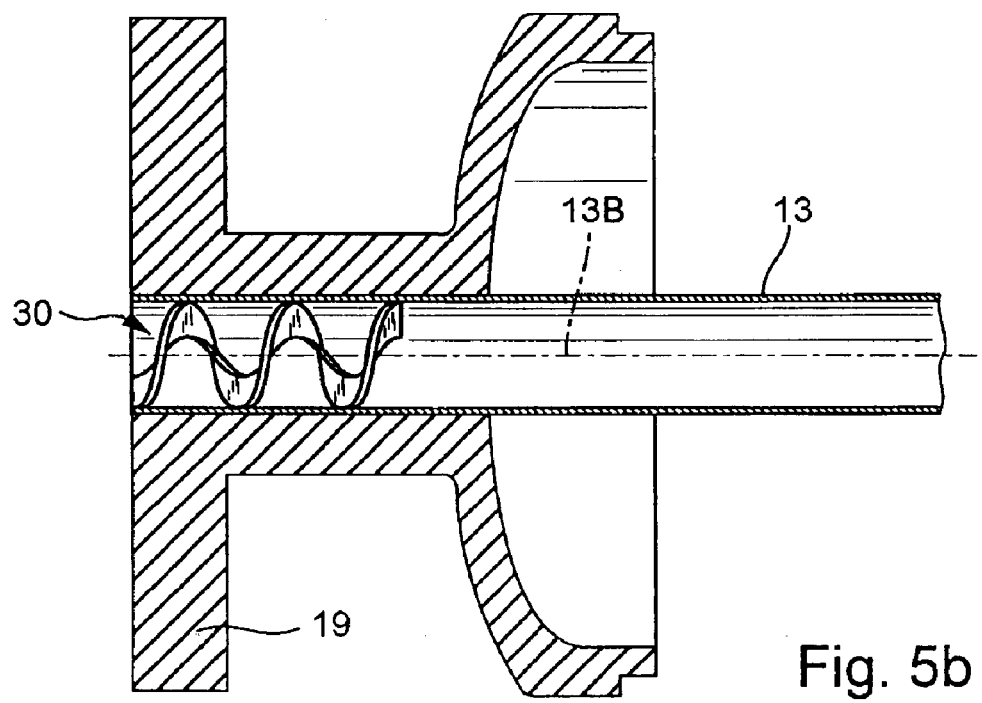
Figure 5C:
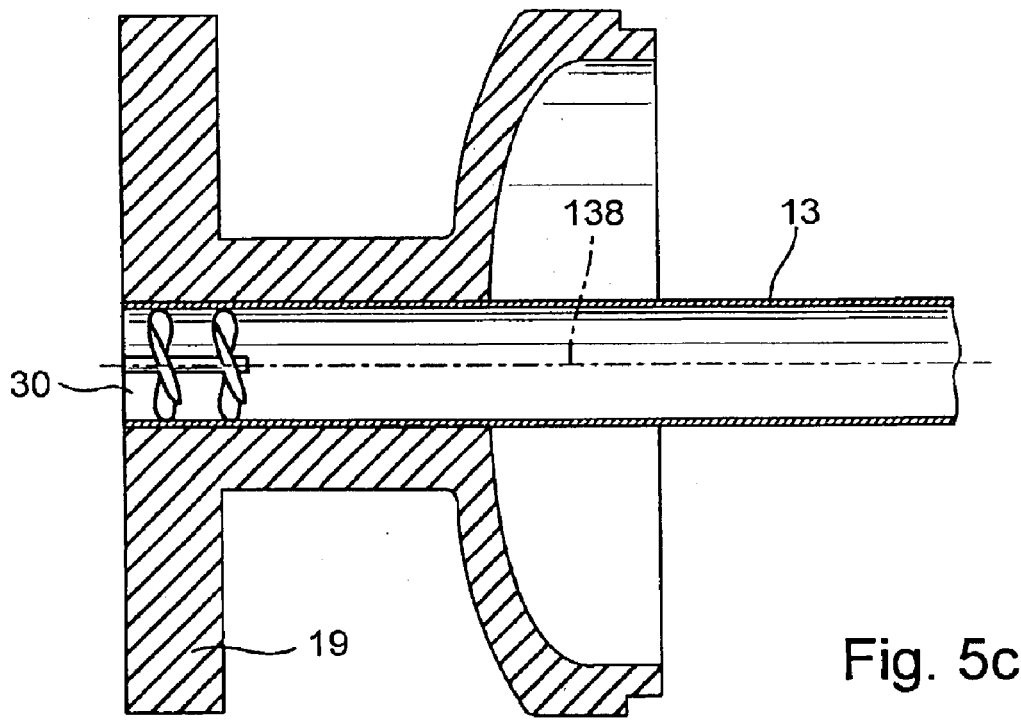

In a embodiment of the invention, the flow-conditioning means for causing the swirl comprise at least one turbulator 30 extending into the flowing fluid. The turbulator 30, which preferably rests in the tube lumen, may be, for instance, a separate propeller-shaped, helical, or helicoidal component which, as indicated in FIGS. 5a to 5d, is disposed at least in part in inlet tube section 13$^+$ or at least in part directly in flow tube 13. Particularly if the means for causing the swirl are in the form of a helical or helicoidal component as shown in FIGS. 5a and 5b, they can be inserted into inlet tube section 13$^+$ and/or flow tube 13 while being subjected to stress, and thus be held by spring force against the respective inside wall.

At this point it should be noted that the means for causing the swirl, particularly the turbulator 30 in the form of a separate component, may also be disposed at least in part within the pipe supplying the fluid to transducer 10. For instance, the turbulator 30 may be disposed within a short pipe section which is separately inserted in the pipe upstream of the transducer 10. Furthermore, the means for causing the swirl may also be formed by a multiply angled section of the pipe, for example.

Figure 5D:
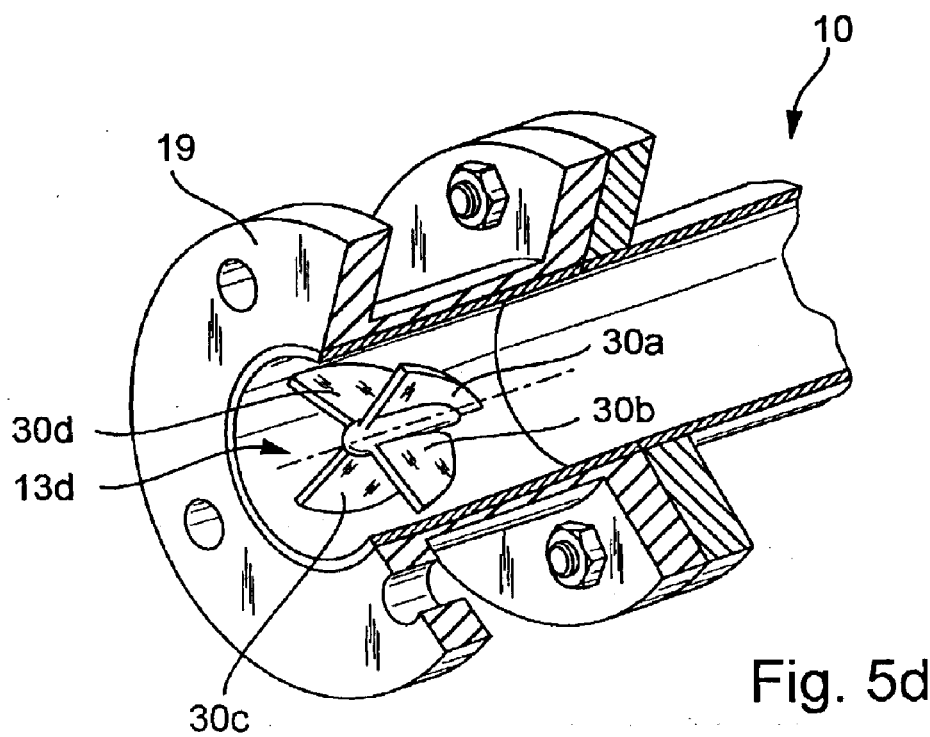

In a further embodiment of the invention, turbulator 30 comprises at least one baffle 30a extending into the flowing fluid at an angle, particularly a baffle formed in the manner of a turbine swirl blade. Preferably, the turbulator comprises two or more such baffles 30a, 30b, 30c, 30d, which, as indicated in FIG. 5d, are so disposed that turbulator 30 takes the form of a guide wheel, for instance of a turbine stator. The at least one baffle 30a is preferably fixed to the inside wall of inlet tube section 13$^+$; if necessary, however, it may also be secured to the inside wall of the fluid-supplying pipe.

In another embodiment of the invention, the means for causing the swirl are designed in the manner of a rifled barrel as a rifling formed in the inside wall of inlet tube section 13$^+$ and/or of flow tube 13.

Investigations have also shown that the means for causing the swirl advantageously should have an effective length in the direction of flow which is at least equal to the nominal diameter of the pipe. Particularly good measurement results were achieved if a reduction in the effective cross-sectional area of inlet tube section 13⁺ and/or of the pipe resulting from the installation of turbulator 30 was either kept very small or compensated for by an increase in the respective nominal cross-sectional area.

A particular advantage of the invention lies in the fact that the transducer using the means for causing the swirl can be operated in virtually any mounting position, particularly also in an essentially horizontal pipe, with essentially unchanged measurement accuracy.

A further advantage is that, if the invention is used in vibratory transducers, the amount of excitation current required to vibrate the flow tube 13, and hence the required amount of energy, is substantially smaller than in conventional transducers, particularly if the fluid to be measured contains a high proportion of gaseous inhomogeneities.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A method of measuring at least one physical parameter, particularly a mass flow rate m and/or a density $\rho$ and/or a viscosity $\eta$, of a fluid flowing in a pipe, the method comprising the steps of:

causing a swirl in a flowing fluid about a swirl axis aligned with a direction of fluid flow for forcing a density distribution in the fluid which is as symmetric with respect to the swirl axis as possible;

causing the fluid rotating about the swirl axis to flow through at least one flow tube of a non-invasive transducer inserted into the pipe, and producing reactions in the fluid corresponding to the parameter to be measured; and sensing reactions in the fluid and generating at least one measurement signal influenced by the parameter to be measured.

2. A method as set forth in claim 1, further comprising the steps of:

vibrating the fluid-conducting flow tube for generating reaction forces in the fluid to be measured which correspond to the parameter to be measured and react on the vibrating flow tube; and sensing vibrations of the flow tube for generating the at least one measurement signal.

3. A transducer for generating a measurement signal corresponding to at least one physical parameter of a fluid flowing in a pipe, the transducer comprising:

at least one flow tube of predeterminable lumen for conducting the fluid, which flow tube communicates at its inlet and outlet ends with the pipe;

an excitation assembly for causing reactions in the fluid within the at least one flow tube, the reactions in the fluid being produced in a non-invasive manner;

a sensor arrangement for sensing the reactions in the fluid and for generating the measurement signal; and means provided in an inlet area of the transducer or at least in the vicinity thereof causing a swirl in the entering fluid and, thus, a rotational motion in the fluid flowing within the flow-tube lumen relative to the flow tube about an axis of rotation lying in the direction of fluid flow.

4. A transducer as set forth in claim 3 wherein the at least one flow tube communicates with the pipe via an inlet tube section and an outlet tube section; and wherein the means for causing the swirl are at least partly disposed within the inlet tube section.

5. A transducer as set forth in claim 3 wherein the means for causing the swirl comprise at least one turbulator extending into the flowing fluid, particularly a stationary turbulator.

6. A transducer as set forth in claim 5 wherein the turbulator comprises at least one baffle extending into the flowing fluid.

7. A transducer as set forth in claim 5 wherein the turbulator has the form of a propeller.

8. A transducer as set forth in claim 5 wherein the turbulator has the form of a propeller.

9. A transducer as set forth in claim 3 wherein during operation, in order to produce reaction forces acting in the fluid, the at least one flow tube is vibrated by means of the excitation assembly; and wherein the vibrations of the flow tube are sensed by means of the sensor arrangement.

10. A meter for measuring at least one physical parameter of a fluid flowing in a pipe, particularly a mass flow rate m and/or a density $\rho$ and/or a viscosity $\eta$, having a transducer comprising: at least one flow tube of predetermined lumen for conducting the fluid, which flow tube communicates at its inlet and outlet ends with the pipe; and excitation assembly for causing reactions in the fluid within the at least on flow tube, the reactions in the fluid being produced in a non-invasive manner; a sensor arrangement for sensing the reactions in the fluid and for generating the measurement signal; and means provided in an inlet area of the transducer or at least in the vicinity thereof which cause a swirl in the entering fluid and, thus, a rotational motion in the fluid flowing within the flow tube lumen relative to the flow tube about an axis of rotation lying in the direction of fluid flow, wherein:

the swirl in the flowing fluid defines a swirl axis aligned with a direction of fluid flow for forcing a density distribution in the fluid which is as symmetric with respect to the swirl axis as possible;

the fluid rotating about the swirl axis is caused to flow through said at least one flow tube of a non-invasive transducer inserted into the pipe, and producing reactions in the fluid corresponding to the parameter to be measured; and reactions are sensed in the fluid and at least one measurement signal is generated which is influenced by the parameter to be measured.

* * * * *

UNITED STATES PATENT AND TRADEMARK OFFICE
CERTIFICATE OF CORRECTION

PATENT NO. : 6,880,410 B2  Page 1 of 1
DATED : April 19, 2005
INVENTOR(S) : Wolfgang Drahm It is certified that error appears in the above-identified patent and that said Letters Patent is hereby corrected as shown below:

Column 12,
Lines 22-23, should read:
-- 8. A transducer as set forth in claim 5 wherein the turbulator is helical, particularly helicoidal. --.

Signed and Sealed this

Seventh Day of February, 2006

JON W. DUDAS
*Director of the United States Patent and Trademark Office*